United States Patent [19]
Whayne et al.

[11] Patent Number: 6,142,993
[45] Date of Patent: Nov. 7, 2000

[54] COLLAPSIBLE SPLINE STRUCTURE USING A BALLOON AS AN EXPANDING ACTUATOR

[75] Inventors: James Whayne, Saratoga; Yi Yang, San Francisco, both of Calif.

[73] Assignee: EP Technologies, Inc., San Jose, Calif.

[21] Appl. No.: 09/032,226

[22] Filed: Feb. 27, 1998

[51] Int. Cl.⁷ .................................................. A61B 18/14
[52] U.S. Cl. ........................... 606/41; 600/374; 600/393; 607/99; 607/113; 607/122
[58] Field of Search ............... 606/41; 600/374, 600/381, 393; 607/99, 113, 122

[56] References Cited

U.S. PATENT DOCUMENTS

| | | | |
|---|---|---|---|
| 5,228,442 | 7/1993 | Imran | 600/374 |
| 5,311,866 | 5/1994 | Kagan et al. | 600/374 |
| 5,465,717 | 11/1995 | Imran et al. | 600/374 |
| 5,782,239 | 7/1998 | Webster, Jr. | 600/374 |
| 5,836,874 | 11/1998 | Swanson et al. | 607/99 |
| 5,891,136 | 4/1999 | McGee et al. | 606/41 |

*Primary Examiner*—Lee Cohen
*Attorney, Agent, or Firm*—Lyon & Lyon LLP

[57] ABSTRACT

A collapsible electrode catheter assembly (10) having a delivery system (12) for controlling a catheter guide tube (16) having a catheter distal end assembly (22) thereon. The catheter distal end assembly (22) has an electrode structure (28) on an expanding assembly (34) for enlarging the electrode structure (28) in an expanded condition. A balloon structure (48) is used to expand and contract the expanding assembly (34) when an inflation medium (64) is alternately introduced into and withdrawn from the balloon structure (48).

16 Claims, 17 Drawing Sheets

| GENERATOR SETTINGS | AVERAGE TEMPERATURE (°C) | | AVERAGE POWER (W) | AVERAGE IMPEDANCE (Ω) | LESION DIAMETER (mm) | LESION DEPTH (mm) |
|---|---|---|---|---|---|---|
| 80W,120s, 80°C | 102a | 78 | 16 | 51 | 15.5 | 7.5 |
| 80W,120s, 80°C | 102b | 78 | 14 | 50 | 16.2 | 8.0 |
| 80W,120s, 80°C | 102c | 78 | 14 | 51 | 13.5 | 6.7 |
| 80W,120s, 80°C | 102d | 77 | 16 | 50 | 14.6 | 7.4 |
| 80W,120s, 80°C | 102e | 77 | 20 | 77 | 14.0 | 8.5 |

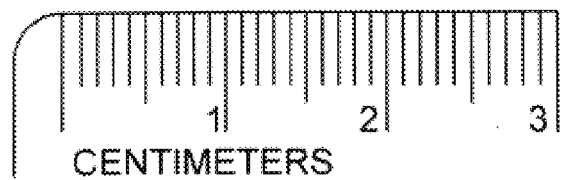
*Fig. 13a*
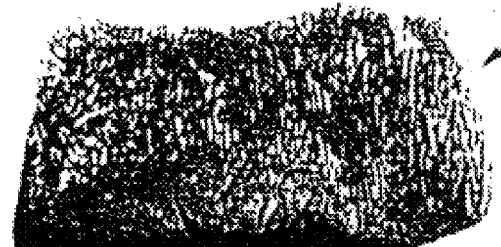
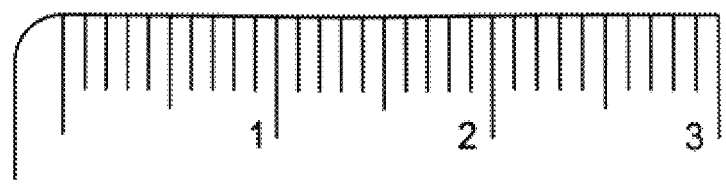
*Fig. 13b*

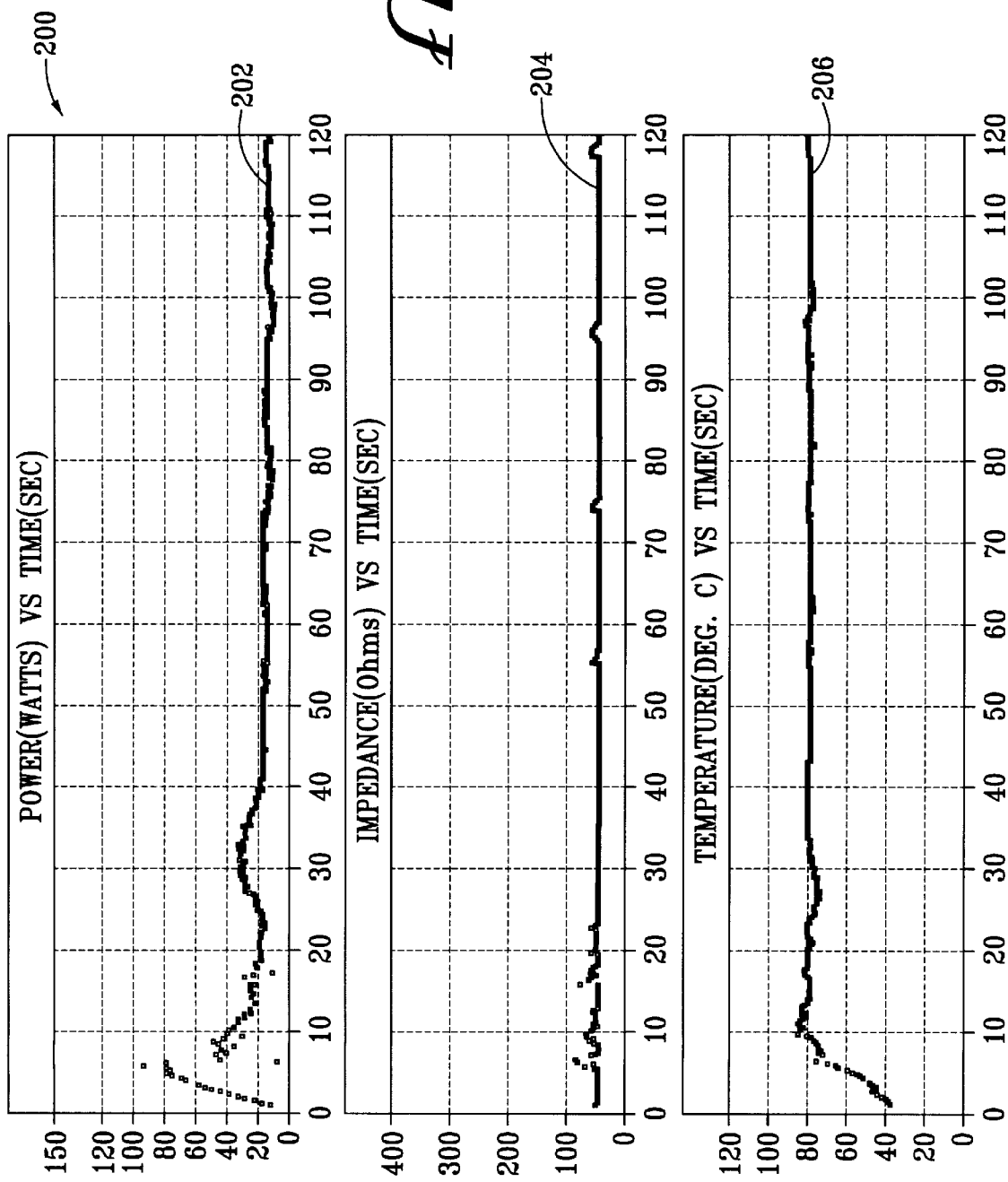

COLLAPSIBLE SPLINE STRUCTURE USING A BALLOON AS AN EXPANDING ACTUATOR

BACKGROUND OF THE INVENTION

1. Field of the Invention

The present invention relates generally to medical catheter devices, and more particularly to tissue ablation catheters having expandable distal end assemblies. The predominant current usage of the inventive ablation catheter with collapsible electrode is in the field of medical catheter surgery in applications wherein it is desirable to produce a lesion of substantial size.

2. Description of the Prior Art

It is known in the medical field that an important method for correcting cardiac fibrillation is to interrupt unwanted potential electrically conductive pathways or "reentry circuits" whereby electrical impulses are misdirected in the heart. This has been done surgically using open heart surgery methods. However such methods are expensive and technically difficult and are, therefore, only rarely attempted. An alternative, and generally superior method has been to accomplish the same result using electrical ablation with the electrodes being introduced into the heart by means of a catheter. A method and means for accomplishing this which is particularly adapted for treating the atria in order to correct atrial fibrillation is taught in U.S. Pat. No. 5,549,661 issued to Kordis et al.

It has been found, however, that related treatment of the ventricles, and of certain other areas of the body as will be discussed in more detail hereinafter, requires a substantially larger area of ablation than is practical using the methods and means described in the Kordis et al. patent referenced above. The largest sized catheter tip to be reliably used intravascularly is referred to as size 8 French. It is known that an 8 French ablation tip generally does not create large enough lesions to ablate VT substrates, especially those positioned intramural or on the epicardial surface. Other technologies including microwave, laser, ultrasound, and chemical ablation are unproven and will require an extensive development process. Fluid cooling technology using RF power and currently available tip sizes increases lesion size by forcing the maximal temperature deeper into the tissue, but this may be accompanied by complications due to "popping" and the resulting thrombi.

Current RF ablation technology has constraints to its lesion creating capabilities. Lesion size is limited by the surface area of the electrode, with theoretical improvements made through fluid cooling the electrode and applying more power through the cooled electrode to force the region of hottest tissue temperature deeper into the tissue. Since cardiac catheter ablation depends on introducing the catheter through preferably an 8F introducer and advancing the ablation catheter tip through the vasculature into the desired heart chamber, size is an important consideration when designing an RF ablation catheter.

It would be desirable to have an ablation catheter which could reliably and safely produce lesions of a size more desirable for the treatment of ventricular conditions. However, to the inventors' knowledge, no such catheter has existed in the prior art. All prior art ablation devices capable of producing the desired lesions have either been too large to introduce through a catheter, or else have required manipulation by the operating physician across the area to be ablated—this last being both difficult and otherwise generally undesirable.

Expandable catheter end portions are known in the art. An example of such is taught in U.S. Pat. No. 5,293,869 issued to Edwards et al., wherein an expandable cardiac probe is used for the purpose of maintaining constant contact with the endocardial surface during expansion and contraction thereof. Balloon catheters are also known in the art, these being used as a general means for enlarging the distal end of a catheter as required. However, to the inventors' knowledge, no catheter having an expandable electrode portion suitable for producing enlarged lesions has been known in the prior art.

DISCLOSURE OF INVENTION

Accordingly, it is an object of the present invention to provide an ablation catheter which will produce lesions of a size sufficient to properly ablate ventricular reentry circuits.

It is another object of the present invention to provide an ablation catheter which will produce relatively large lesions, as required, in essentially any area of the body which can be reached via a catheter.

It is yet another object of the present invention to provide an ablation device which is small enough, both during entry and removal, to be safely introduced into the ventricle through a catheter.

It is still another object of the present invention to provide an ablation catheter which will reliably, consistently and controllably produce lesions of a desired size.

It is yet another object of the present invention to provide an ablation catheter design which can be readily constructed to produce instruments of consistent quality and characteristics.

Briefly, the present inventive catheter ablation device has a collapsible ablation electrode such that the electrode is introduced and withdrawn through the catheter in a collapsed state and further such that the electrode will produce a sizable lesion when expanded. In a preferred embodiment of the invention, collapsible spline structures are expanded using a balloon structure having an electrode structure superimposed thereon. In equally preferred alternative embodiments of the invention various combinations and arrangements of electrodes and sensors are placed and arranged such that an effective surface area thereof is caused to expand by the inflation of the balloon structure. In yet another equally preferred alternative embodiment the collapsible ablation structure involves the use of a catheter a distal section which positions the ablation electrodes to bring the ablation electrodes close enough to take advantage of the additive effects to produce large and/or deep lesions.

It is an advantage of the present invention that relatively large lesions can be produced in the body generally wherever such lesions are desired and where a catheter can be introduced thereto.

It is yet another advantage of the present invention that a relatively large electrode can be collapsed both for introduction and removal through a catheter.

It is still another advantage of the invention that reliably consistent results can be obtained in the production of relatively large lesions.

It is yet another advantage of the invention that open heart surgery can be avoided in many instances.

These and other objects and advantages of the present invention will become clear to those skilled in the art in view of the description of the best presently known mode of carrying out the invention and the industrial applicability of the preferred embodiment as described herein and as illustrated in the several figures of the drawing.

BRIEF DESCRIPTION OF THE DRAWINGS

FIG. 11b is a side cross sectional view of the first tissue sample and first lesion of FIG. 11a;

FIG. 12b is a side cross sectional view of the second tissue sample and second lesion of FIG. 12a;

FIG. 13a is a perspective view of a third in vitro tissue sample showing a third lesion made experimentally therein;

FIG. 13b is a side cross sectional view of the third tissue sample and third lesion of FIG. 13a;

FIG. 14b is a side cross sectional view of the fourth tissue sample and fourth lesion of FIG. 14a;

FIG. 15b is a side cross sectional view of the fifth tissue sample and fifth lesion of FIG. 15a;

FIG. 20 is a time line chart showing the power, impedance and temperature of the inventive expandable electrode catheter over time during the course of the experiment shown in FIGS. 15a.

BEST MODE FOR CARRYING OUT INVENTION

Figure 1:
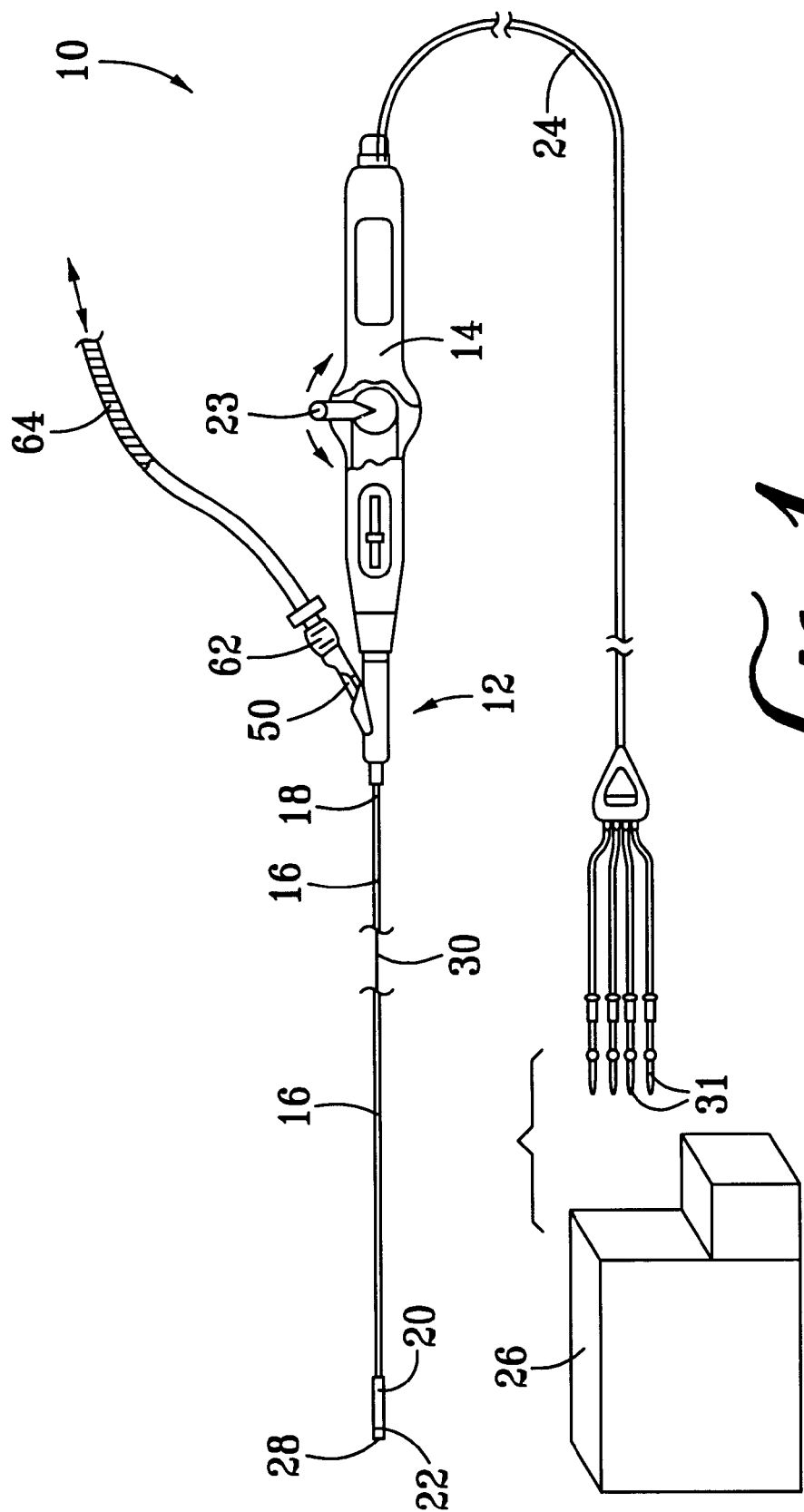
FIG. 1 is a perspective view of a preferred embodiment of the present invention showing a delivery system therefor and the relationship of the inventive portion thereto.

The best presently known mode for carrying out the invention is a collapsible electrode catheter assembly. The inventive collapsible electrode catheter assembly is depicted in a perspective view in FIG. 1 and is designated therein by the general reference character 10. The collapsible electrode catheter assembly 10 has a delivery system 12 which, in many respects, is not unlike known related devices in the field. The delivery system 12 has a handle 14, and a guide tube 16 having a proximal end 18 that is engaged to the handle 14 and a distal end 20. A catheter distal end assembly 22 is engaged to the distal end 20 of the guide tube 16. A steering handle 23 is provided on the handle 14 for guiding the catheter distal end assembly 22 into position. The use of the steering handle 23 and techniques for positioning the catheter distal end assembly 22 will be known to one skilled in the art of catheter surgery. An electrical cable 24 interconnects a system controller 26 to the proximal end of the handle 14. As will be described in detail hereinafter, the catheter distal end assembly 22 has an electrode structure 28 having a geometry that is controlled to expand or collapse according to the present inventive structure and method of operation thereof.

The electrode structure 28 of the catheter distal end assembly 22 is electrically connected by lead wires 30 that pass through the guide tube 16 to the handle 14 and are ultimately interconnected to the system controller 26 via the electrical cable 24 and electrical connectors 31. The system controller 26 is utilizable to provide controlled electrical power to the electrode structure 28 and, where applicable, to process electrical signals from the electrode structure 28, as will be discussed in greater detail hereinafter.

Figure 2:
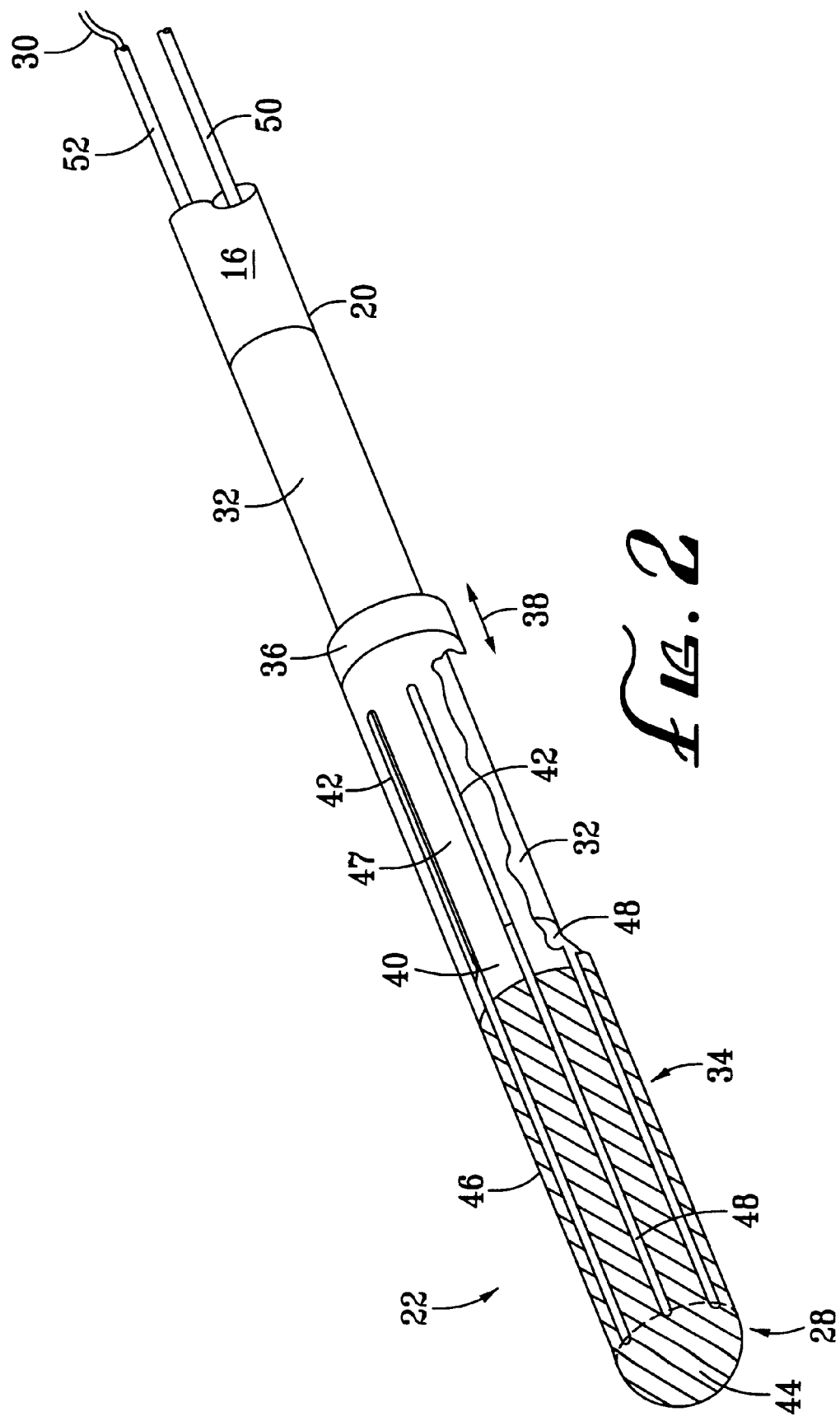
FIG. 2 is a more detailed perspective view, partially cut away, of the catheter distal end assembly shown in FIG. 1 in its collapsed state.

FIG. 2 shows the catheter distal end assembly 22 of FIG. 1 in greater detail as compared to the view of FIG. 1. As seen in the view of FIG. 2, the catheter distal end assembly 22 is in a collapsed state suitable for introducing and removing the catheter distal end assembly 22 intravascularly. The catheter distal end assembly 22, as depicted in the view of FIG. 2, has the electrode structure 28 disposed generally toward the distal end thereof. The catheter distal end assembly 22 has a main body 32 affixed to and extending from the distal end 20 of the guide tube 16. (Indeed, it is within the scope of the invention that the main body 32 may, in fact, be the end of the guide tube 16, itself.) An expanding assembly 34 has a guide collar 36 which is free to move linearly, as is indicated by a guide collar movement arrow 38 in the view of FIG. 2, along the main body 32 as the expanding assembly 34 is expanded and contracted. As can be seen in the cut away portion of FIG. 2, in this embodiment of the invention the main body 32 extends into a substantial portion of the expanding assembly 34 such that the guide collar 36 does not slip off of the main body 32 as the guide collar 36 moves toward the distal end of the main body 32.

A plurality of splines 40 are created in the expanding assembly 34 by the removal of material from the expanding assembly 34 to create a plurality of slots 42 therein. In the example of FIG. 2 there are eight splines 40 (four of which are visible in the view of FIG. 2) and eight slots 42 (three of which are visible in the view of FIG. 2), although these quantities are subject to variance, as will be discussed in greater detail hereinafter. A cap portion 44 is located at the distal end of the expanding assembly 34 for joining the splines 40 at that end. As can be seen in the view of FIG. 2, the cap portion is rounded such that the catheter distal end assembly 22 can readily be introduced intravascularly without unnecessarily damaging vascular tissue. The electrode structure 28 can be seen to cover the cap portion 44 of the expanding assembly 34 and a conductive portion 46 of the splines 40. A non-conductive substrate 47 of the splines 40 can be seen in the view of FIG. 2 where the electrode structure 28 is not superimposed on the splines 40. A balloon structure 48 can be seen in a deflated state through the slots 42 of the expanding assembly 34. In the first preferred embodiment 22 of the inventive cathode distal end assembly, as depicted in the view of FIG. 2, a balloon inflation lumen 50 is provided whereby the balloon 48 can be inflated by the introduction of inflating fluid therethrough, as will be discussed in greater detail hereinafter. A lumen 52 is provided for enclosing the lead wires 30 discussed previously herein in relation to FIG. 1.

Figure 3:
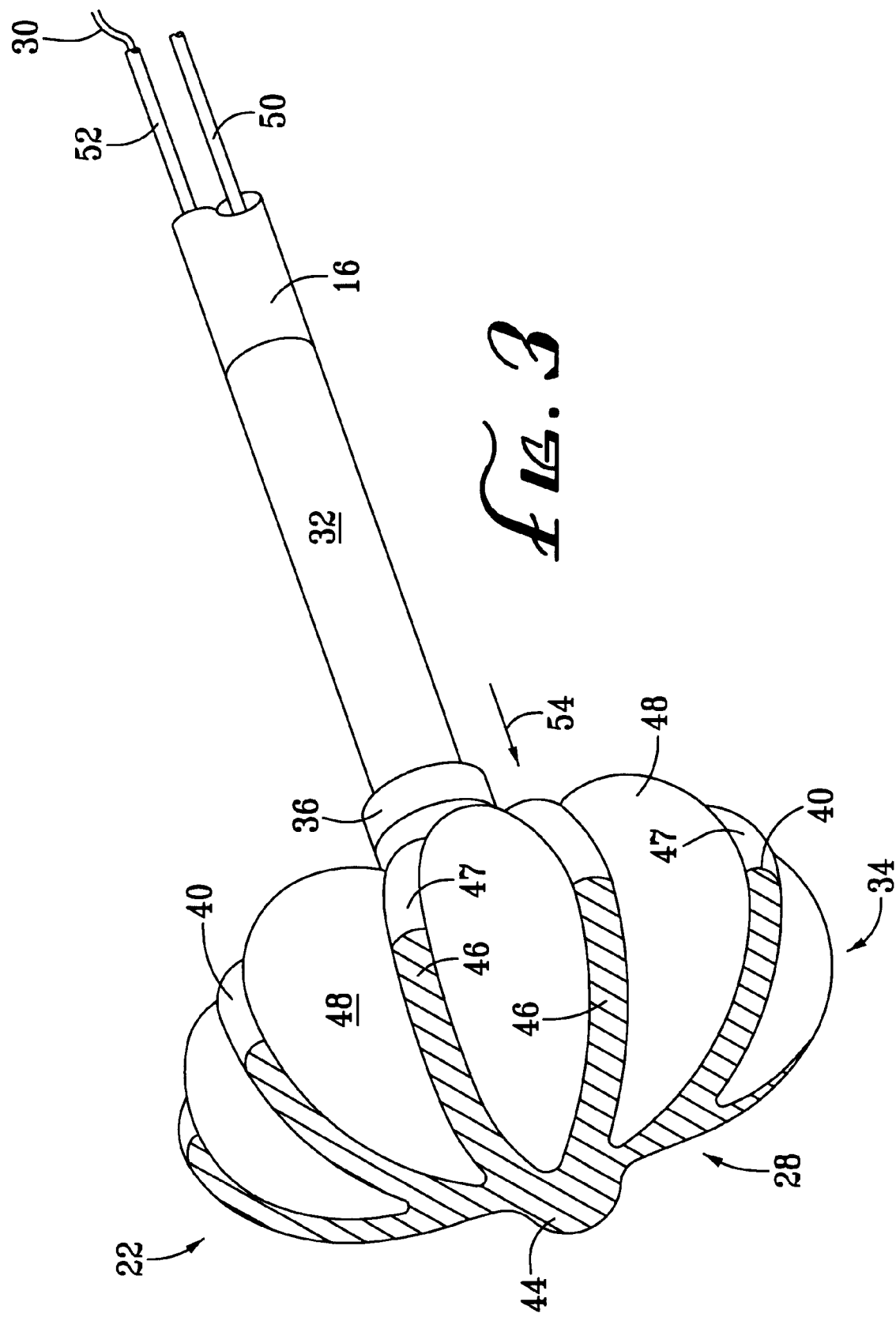
FIG. 3 is a perspective view showing the catheter distal end assembly of FIG. 2 in an expanded state.

FIG. 3 is a perspective view showing the catheter distal end assembly of FIG. 2 in an expanded state. To achieve the state depicted in the view of FIG. 3 an inflating fluid is introduced through the balloon inflation lumen 50 to expand the balloon structure 48 such that the splines 40 are forced apart and generally into the curved shape depicted in the view of FIG. 3. In this embodiment of the invention, the cap portion 44 of the expanding assembly 34 is affixed internally to the distal end of the balloon structure 48 such that the expansion of the balloon structure 48 causes the guide collar 36 to slide along the main body 32 toward the distal end thereof in the direction indicated by a directional arrow 54 to attain the position depicted in the view of FIG. 3. In this embodiment the attachment of the expanding assembly 34 to the distal end of the balloon structure 48 is accomplished by an adhesive (not shown), although other attachment methods, such as heat bonding, are also equally applicable. It should be noted that the conductive cap portion 44 and the conductive portion 46 of the splines 40 constitute the electrode structure 28 in the first preferred embodiment 22 of the catheter distal end assembly as described herein.

Figure 4:
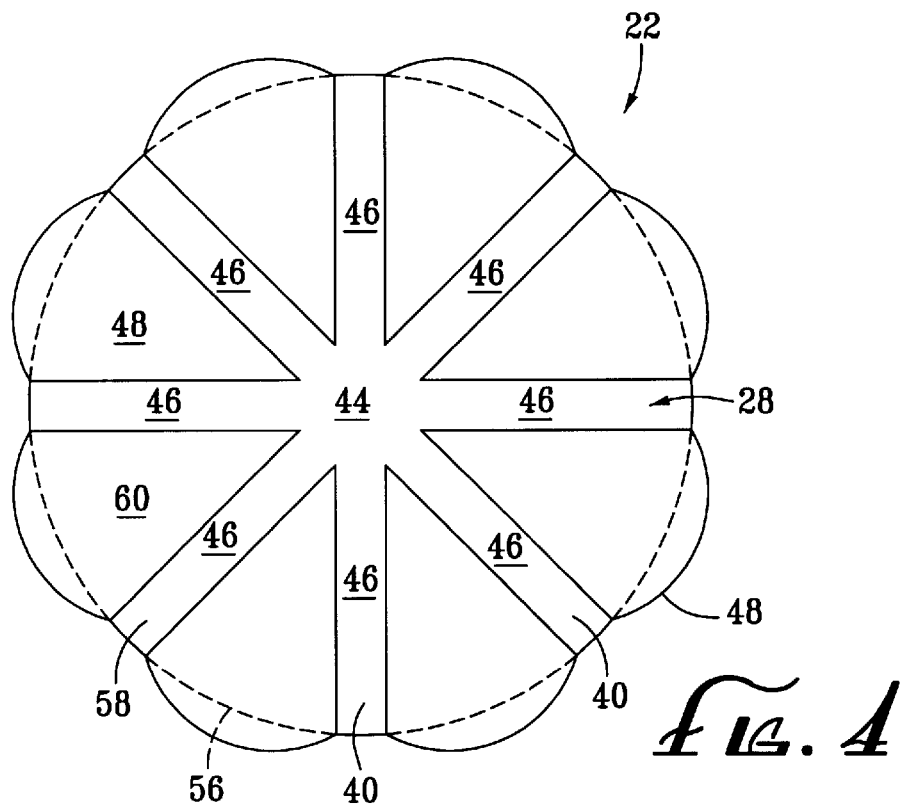
FIG. 4 is an end view of the catheter distal end assembly in the inflated condition as depicted in the view of FIG. 3.

FIG. 4 is an end view of the catheter distal end assembly 22 in the expanded condition as depicted also in the view of FIG. 3. In the view of FIG. 4, only a part of the conductive portion 46 of the splines 40 is visible, the nonconductive portion 47 thereof being obscured behind the curve of the balloon structure 48 in this view. An imaginary circle indicated by a dotted line in the view of FIG. 4 describes an intended contact area 56 of the electrode structure 28, which is that portion of the electrode structure 28 and adjacent portions of the balloon structure 48 which are expected to come into effective contact with tissue to be ablated. While it is anticipated that there may be numerous dimensional aspects and variations in the shape of the electrode structure 28 as might be appropriate to different applications, the inventors have determined that a size 8F catheter distal end assembly 22 according to the best presently known embodiment 10 of the present invention will have eight splines 40 and the total contact area 56 will be approximately 0.1960 square inches (4.978 mm$^2$). A conductive portion 58 of the contact area 56 (being that portion of the electrode structure 28 which lies within the contact area 56) will, then, constitute approximately 0.0848 square inches (2.154 mm$^2$) which is approximately 43.3% of the total contact area 56. A non conductive portion 60 of the contact area (which will be that portion of the balloon structure 48 which is lying within the contact area 56 and further which does not have the electrode structure 28 superimposed thereon) will, therefore, be approximately 0.1112 square inches (2.824 mm$^2$), which is approximately 56.7% of the total contact area 56.

Figure 5:
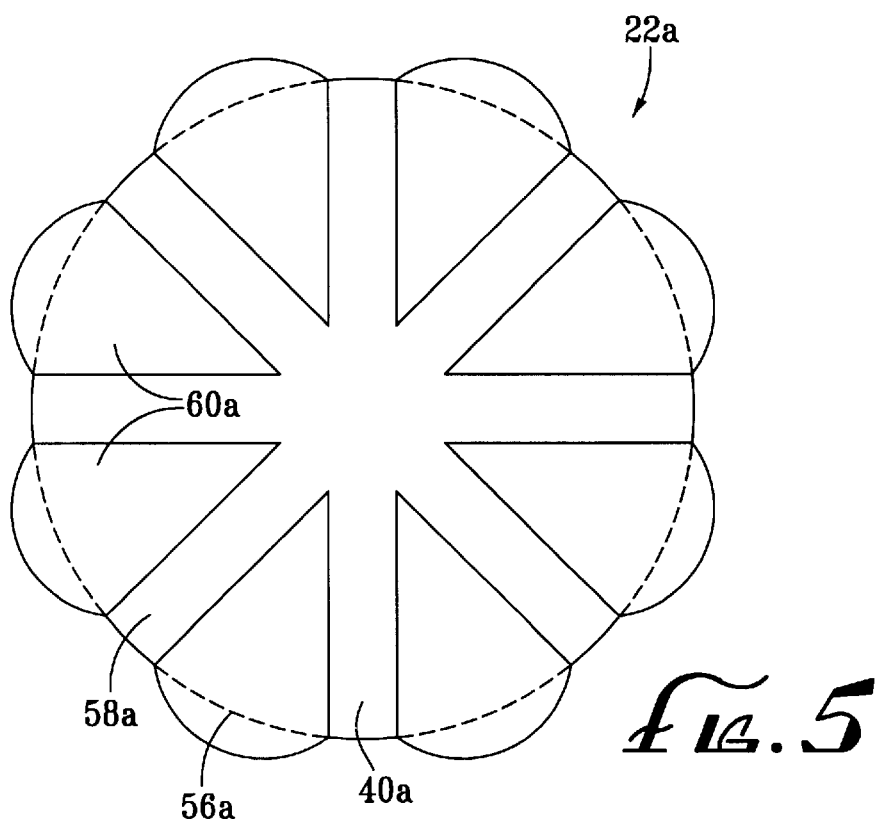
FIG. 5 is an end view of an alternate size catheter distal end assembly, similar to the view of FIG. 4, showing possible alternate dimensions for this embodiment of the invention.

FIG. 5 is an end view, similar to the view of FIG. 4, of an alternate size catheter distal end assembly 22a according to the first preferred embodiment of the invention. The alternate size catheter distal end assembly 22a is presented herein merely as an example of how the first preferred catheter distal end assembly 22 might be produced in alternate sizes and dimensionalities. The example of FIG. 5 illustrates a size 10F alternate size catheter distal end assembly 22a such as might be produced for applications where such a relatively large size could be accommodated. In the example of the alternate size distal end assembly 22a, the inventors propose that, with the quantity of splines 40a being eight, an alternate contact area 56a will have a total area of approximately 0.1960 square inches (4.978 mm$^2$) while an alternate conductive portion 58a of the alternate contact area 56a will have an exposed area of 0.0984 square inches (2.499 mm$^2$) (approximately 50.2% of the total alternate contact area 56a), and an alternate non conductive portion 60a of the alternate contact area 56a will have an area of approximately 0.0976 square inches (2.479 mm$^2$) (approximately 49.8% of the total alternate contact area 56a).

Regarding the materials of the catheter distal end assembly 22 and the alternate size catheter distal end assembly 22a, the balloon structure 48 is made from a material selected to exhibit the following characteristics:

(i) the material must be capable, in use, of transition between an expanded geometry having a first maximum diameter and a collapsed geometry having a second maximum diameter less than the first diameter. In this respect, the material can be formed into the expandable-collapsible bladder or balloon structure 48 having an open interior. In alternative embodiments and/or potential future modifications of the inventive collapsible electrode catheter assembly 10, as will be discussed in more detail hereinafter, the expanding assembly 34 (or equivalent thereof) is made flexible enough to assume the expanded geometry as a result of a normally open solid support structure within the interior, or the opening of a normally closed support structure within the interior, or the introduction of fluid pressure into the interior, or a combination of such interior forces. In this arrangement, the body is caused to assume the collapsed geometry by an exterior compression force against the normally open interior support structure, or the closing of the interior support structure, or the removal of the interior fluid pressure, or a combination of such offsetting forces. Alternatively, the material can be a preformed body with a memory urging it toward a normally expanded geometry. In this arrangement, the preformed body can have an open interior, or can comprise, for example, a collapsible composite foam structure.

(ii) the material should be biocompatible and able to withstand high temperature conditions, which arise during the manufacture and use thereof.

(iii) the material should possess sufficient strength to withstand, without rupture or tearing, external mechanical or fluid forces, which are applied to support and maintain its preformed geometry during use.

(iv) the material should lend itself to attachment to the main body 32 through the use of straightforward and inexpensive adhesive, thermal or mechanical attachment methods.

(v) the material should be compatible with the materials of the remainder of the expanding assembly 34 to achieve secure adherence between those portions of the expanding assembly 34 to which the balloon structure 48 will be required to adhere.

Thermoplastic or elastomeric materials that can be made to meet these criteria include polyester, silicone rubber, nylon, polyethelene, polyvinyl chloride, and composite structures using these and/or other materials.

The incidence of tissue sticking to the exterior of the catheter distal end assembly 22 during use can be mediated by the inclusion of low friction materials like PTFE. The propensity of the exterior of the catheter distal end assembly 22 to cause blood clotting and/or embolization can be reduced by incorporating non-thrombogenic material onto or into the exterior of the catheter distal end assembly 22.

Silicone is particularly preferred for the balloon structure 48 of the expanding assembly 34. Silicone is flexible and elastic. It can withstand very high temperatures without deformation.

It should be remembered that it is important that the expanding assembly 34 be returned to its original size (or nearly so) such that the catheter distal end assembly 22 can be withdrawn after the surgical procedure is completed. Therefore, it is anticipated that the use of materials having a memory shape will be beneficial in the construction of the splines 40 and related portions of the expanding assembly 34, as well as in the balloon structure 48 itself.

In the embodiments shown in FIGS. 2 through 5, fluid pressure is used to inflate and maintain the expandable-collapsible body 22 in the expanded geometry. In this arrangement, as discussed briefly herebefore in relation to FIG. 2, the catheter guide tube 16 carries the balloon inflation lumen 50 in addition to the lumen 52 along its entire length. The distal end of the balloon inflation lumen 50 lumen opens into the hollow interior of the balloon structure 48, which has been formed in the manner just described.

Referring again to the view of FIG. 1, it can now be appreciated that the balloon inflation lumen 50, which has been discussed previously herein in relation to the view of FIG. 3, passes through the catheter guide tube 16 from the catheter distal end assembly 22 and the proximal end of the balloon inflation lumen 50 communicates inside the handle 14 with a fluid port 62 on the handle 14.

An inflation fluid medium 64 is conveyed under positive pressure through the fluid port 62 and into the balloon inflation lumen 50. The fluid medium 64 exerts interior pressure to urge the balloon structure 48 (FIGS. 2 and 3), and thus the entire expanding assembly 34, from the collapsed geometry as illustrated and discussed in relation to FIG. 2 to the enlarged geometry desired for ablation, as has been illustrated and discussed in relation to FIG. 3.

The inflating fluid medium 64 can vary. Preferably, it comprises a liquid such as water, saline solution, or other biocompatible fluid. In the best presently known embodiment 10 of the present invention, the inflating medium 64 is a liquid saline solution. Alternatively, the inflating fluid medium 64 could be a gaseous medium such as carbon dioxide or air.

Figure 6:
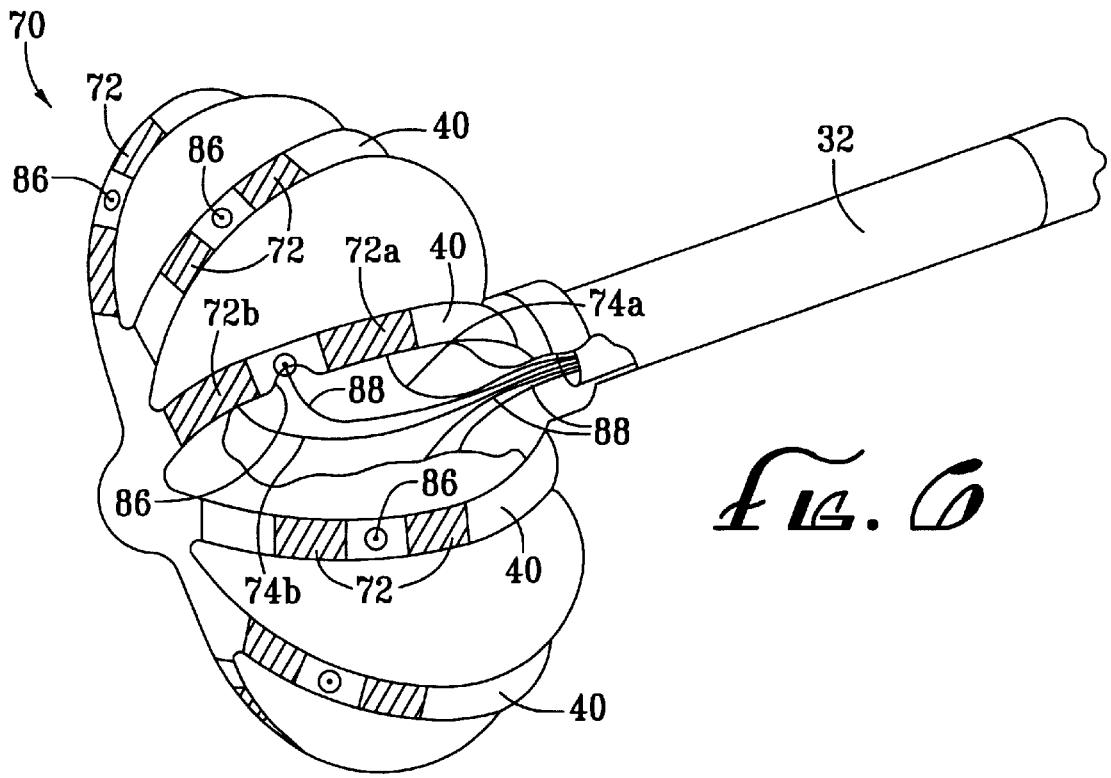
FIG. 6 is a perspective view of an equally preferred alternate embodiment of the inventive catheter distal end assembly, in an expanded state.

FIG. 6 is a perspective view of an equally preferred alternate embodiment 70 of the present invention, shown in the expanded condition. It should be noted that the first preferred catheter distal end assembly 22 of this invention, as discussed previously herein, has but the single electrode structure 28, thus constituting a unipolar device. One skilled in the art will recognize that this arrangement will generally require the use of a second electrode located either inside or outside the body, and such devices and related procedures are known in the art. Alternatively, however, the equally preferred alternate embodiment 70 illustrated in FIG. 6, while otherwise similar in construction to the embodiments described in relation to FIGS. 2 through 5, has a plurality of individual electrodes 72 separately dispersed along the splines 40 of the alternate catheter distal end assembly 70. The individual electrodes 72 allow the connection, for example of a first wire 74a to a first individual electrode 72a and a second wire 72b to a second individual electrode 72b, with the remainder of the individual electrodes 72 for which the wiring is not visible in the view of FIG. 6 being alternately wired in like manner. In this arrangement, RF power can be applied to the first individual electrode 72a and some of the other electrodes 72, while the second individual electrode 72b and other of the electrodes 72 act as a ground electrode. It should be noted that the specific arrangement and wiring of the individual electrodes 72 shown in FIG. 6 and discussed herein is presented by way of example only. Alternately, each of the individual electrodes 72 could be separately wired and powered such that the alternate catheter distal end assembly depicted in FIG. 6 could be used as a unipolar device (with a separate external electrode as in the manner discussed previously herein in relation to the first preferred catheter distal end assembly 22). Such an arrangement would allow the separate control of each of the individual electrodes 72. Yet another application of the alternate catheter distal end assembly 70 would be to provide phased power to the individual electrodes 72 such that each of the individual electrodes 72 would be slightly out of phase with adjacent individual electrodes 72. It is anticipated by the inventors that many various arrangements and combinations of the individual electrodes 72 will prove to be useful.

Figure 7:
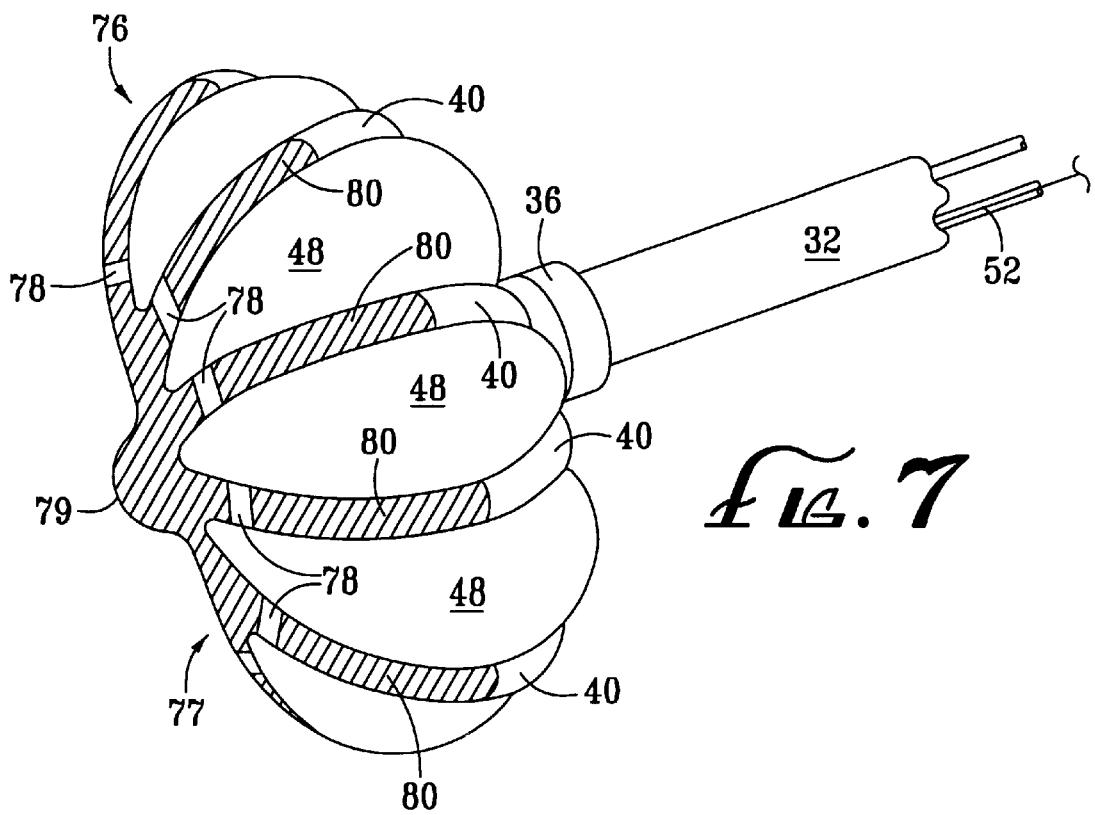
FIG. 7 is a perspective view of another equally preferred alternate embodiment of the inventive catheter distal end assembly, in an expanded state.

FIG. 7 is a perspective view, also shown in an expanded condition, of a second equally preferred alternate embodiment 80 of the invention. The second alternate catheter distal end assembly 82 is similar in construction to the first preferred catheter distal end assembly 22, having the similar balloon structure, splines, 40, guide collar 36 and main body 32 as discussed previously herein. However, an alternate electrode structure 77 has a plurality (one per spline 40 in the example of this embodiment) of nonconductive gaps 78 in the electrical coating which constitutes the alternate electrode structure 77. The gaps 78 separate an end cap electrode 79 from a plurality (one per spline 40 in the example of this embodiment) of spline electrodes 80. This enables each of the thus separated electrodes 79 and 80 to be separately wired and powered for better individual and overall control of the heat distribution in the area of tissue to be ablated.

Referring again to the view of FIG. 6, it is anticipated that many, if not most, of the applications of the present invention will require the use of temperature sensors for feeding back information to the physician and/or to the system controller such that temperature of the electrodes 72 can be more precisely controlled. Therefore, by way of example, a plurality of sensors 86 (one per spline 40, in the example of FIG. 6) are attached to the splines 40 near the individual electrodes 72. The sensors 86 will send their signals back to the system controller 26 (FIG. 1) via a plurality (one per sensor 86) of sensor wires 88 which will pass through, in this embodiment, the lumen 52. For the sake of clarity, not all of the sensor wires 88 are shown in the view of FIG. 6. The sensors 86 are used to determine when sufficient energy has been applied to accomplish the desired ablation and/or as a backup safety device to stop the further application of energy when a dangerously high temperature is detected. It should be noted that the quantity and placement of the sensors 86 as illustrated in FIG. 6 is intended as an example only, as it is anticipated that the quantity and placement of the sensors 86 will be adapted according to the needs of various applications of the invention. Furthermore, it should be noted that, although the sensors 86 are illustrated in FIG. 6 as being placed on an embodiment similar to the alternate catheter distal end assembly 70, it is anticipated that the addition of the sensors 86 will be applicable to essentially any conceivable embodiment of the invention.

Figure 8:
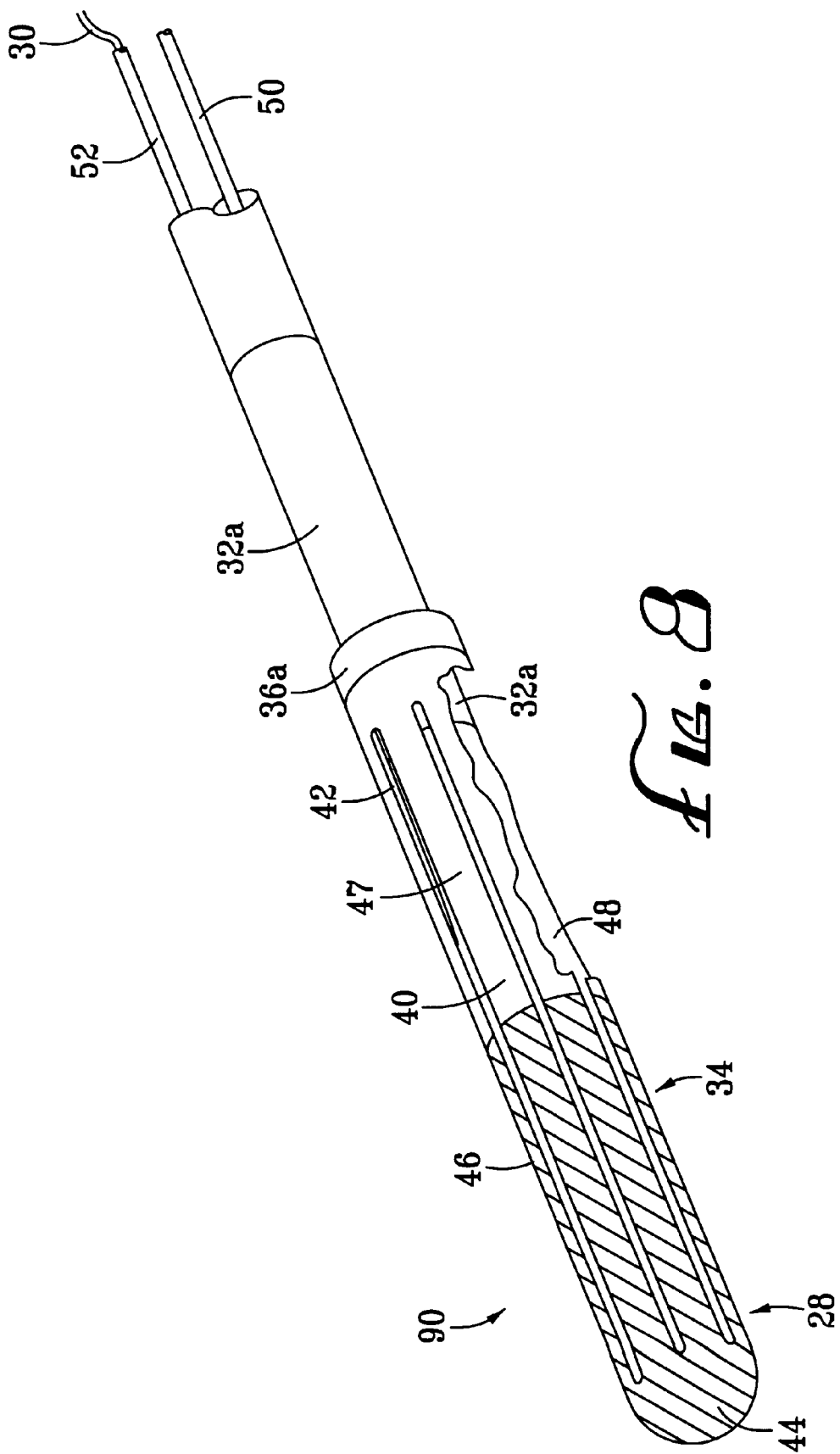
FIG. 8 is a partially cut away perspective view of yet another equally preferred alternate embodiment of the inventive catheter distal end assembly, in an collapsed state.

FIG. 8 is a partially cut away perspective drawing showing a third alternate catheter distal end assembly 90 in its deflated, or collapsed, state. The third alternate catheter distal end assembly 90 is not greatly unlike the first preferred embodiment 22 of the inventive catheter distal end assembly. A significant difference can be seen in the cut away portion of the drawing of FIG. 8, wherein it is evident that an alternate main body 32a of the third alternate catheter distal end assembly 90 extends only a relatively little way into the expanding assembly 34. Also, whereas the guide collar 36 (FIG. 2) of the first preferred catheter distal end assembly 22 is free to slide along the main body 32 as indicated by the directional arrow 38, in the third alternate catheter distal end assembly 90 (FIG. 8) an alternate collar 36a is immovably affixed (by an adhesive in this embodiment, although other attachment methods are applicable) to the alternate main body 32a. It should be noted that, according to the embodiment of the third alternate catheter distal end assembly 90, balloon structure 48 is not attached directly to the expanding assembly 34.

Figures 9, 10:
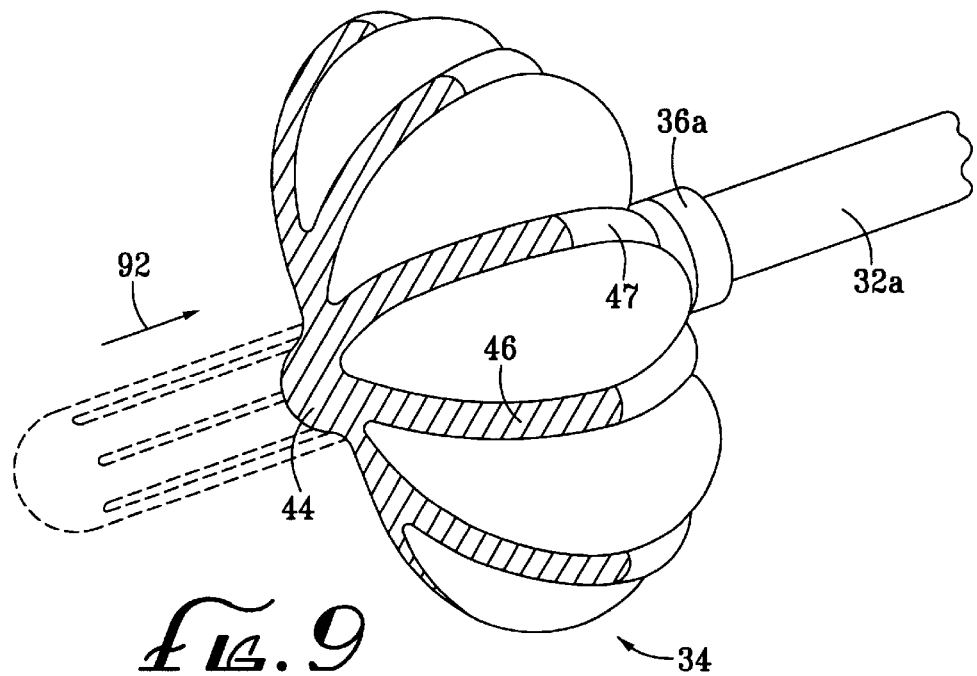
FIG. 9 is a perspective view of the alternate embodiment of the invention illustrated in FIG. 8, in an expanded state.
FIG. 10 is a data chart showing the conditions and results of in vitro testing performed to establish a best presently known embodiment of the present inventive method.

FIG. 9 is a perspective view of the third alternate catheter distal end assembly 90 in its expanded state. As can be seen by comparing the view of FIG. 9 with that of FIG. 3, the inflated state of the third alternate catheter distal end assembly 90 is much like the inflated state of the first preferred catheter distal end assembly 22—the principle exception being that, in order to achieve the expanded state, the end cap portion 44 of the third alternate catheter distal end assembly 90 has moved proximally the direction indicated by a directional arrow 92.

Various modifications may be made to the invention without altering its value or scope. For example, in addition to the various expanding devices described specifically herein, it is anticipated that other expanding/contracting structures will readily be produced to cause the desired expansion and contraction of the electrode structure 28. These have been discussed previously herein in relation to the applicable materials which might be applied to the purpose. Yet another likely modification would be to add further sensing or guidance devices to the delivery system 12.

Industrial Applicability

The collapsible electrode catheter assembly 10, and related embodiments described herein, will create a very large lesion using radio frequency current capable of ablating substrates causing ventricular tachycardia. Yet at the same time, it has a small introductory and withdrawal profile. In vitro evaluations of the collapsible spline catheter show resulting lesion sizes sufficient to cure intramural and/or epicardial VT substrates. This includes the option to create large, deep lesions and/or wide, shallow lesions. Furthermore, using the balloon structure 48 as the expanding actuator not only allows the physician to deploy the collapsible spline structure of the expanding assembly 34 at will and consistently, but also provides radial and lateral support for the expanding assembly, thus allowing better tissue contact with the expanded splines 40.

The inherent structure and the use of long, small diameter ablation elements to create large lesions, as described herein, is a new and important development in the field. The use of the balloon structure 48 as an actuator to expand the long, small diameter ablation electrode structure 28 is new. In addition, the ability to use such a structure in conjunction with simultaneous energy delivery to bridge gaps, and the advantage of controlling edge effects by structure design to direct the energy delivery are important advances of the present invention.

FIG. 10 is a data chart 100 summarizing the conditions and results of in vitro testing done to determine a best presently known embodiment of the present inventive method. Each horizontal line 102a through 102e of the data chart 100 discloses the conditions and results for an individual test relevant to this determination. As can be seen from a reading of the data chart 100, the externally controllable conditions (the generator settings) for each of the tests described in lines 102a through 102e are identical, these being the conditions according to the best presently known embodiment of the method.

Figure 11A:
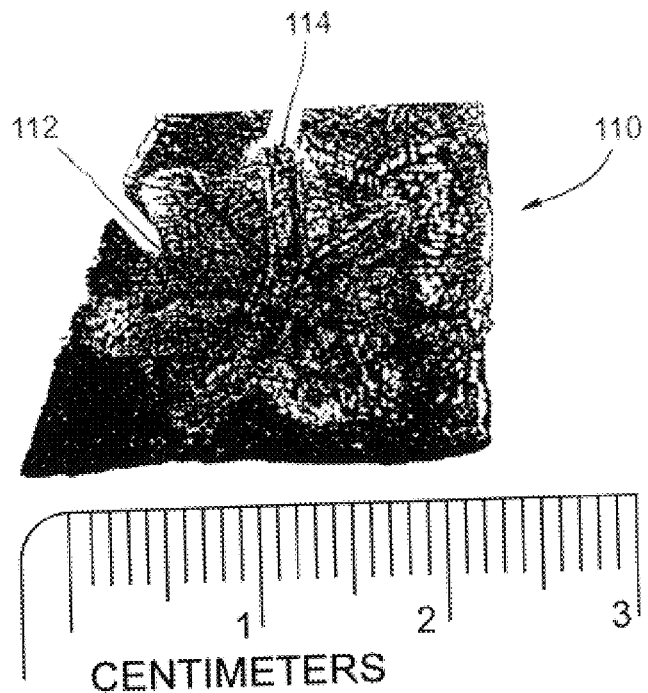
FIG. 11a is a perspective view of a first in vitro tissue sample showing a first lesion made experimentally therein.
Figure 11B:
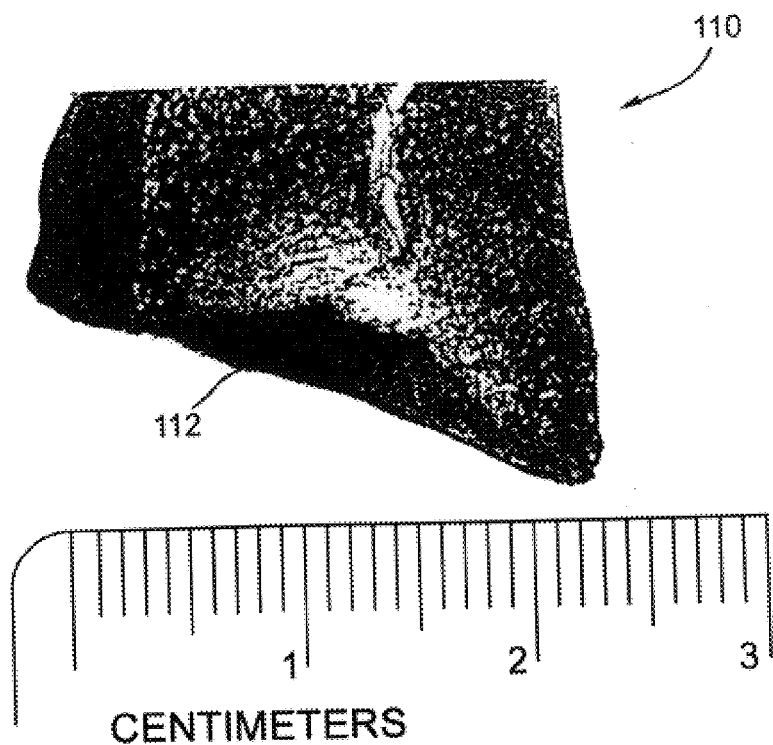

FIG. 11a is a perspective view of a first tissue sample 110 with a first lesion 112 created according to the conditions described in line 102a of the data chart 100 (FIG. 10) therein. As can be seen in the view of FIG. 11a, the lesion 110 has a star portion 114 within the overall lesion 112. The star portion 114 corresponds generally to the area of the tissue sample 110 contacted directly by the electrode structure 28 (FIG. 3). It should be noted that the overall lesion 112 is relatively regular in shape, there being no significant gaps in the lesion 112 between the various aspects of the star portion 114 of the lesion. FIG. 11b is a side cross sectional view of the tissue sample 110 of FIG. 11a showing the depth of the first lesion 112 in the first tissue sample 110 as recorded in the first line 102a of the data chart 110 (FIG. 10).

Figure 12A:
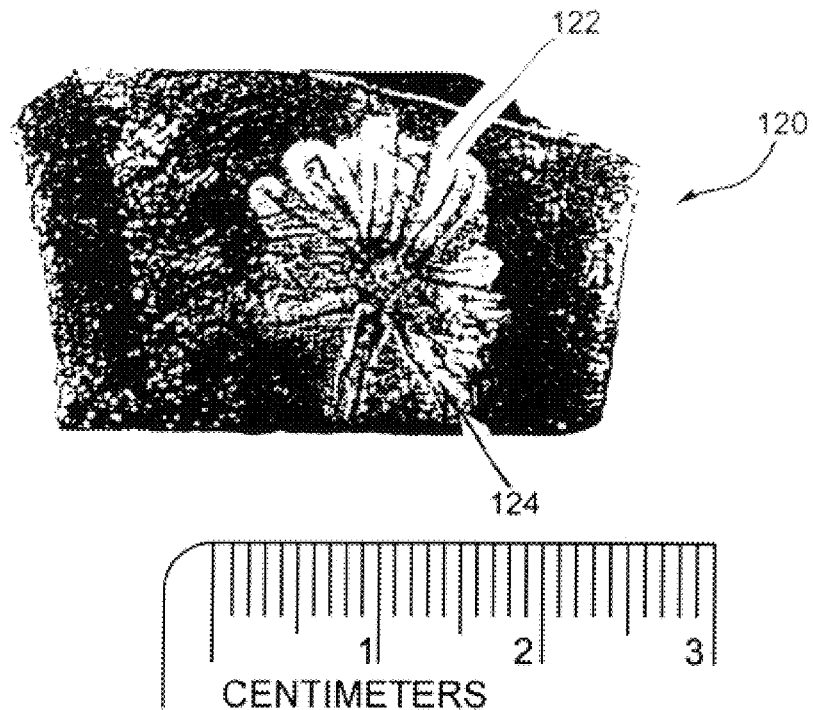
FIG. 12a is a perspective view of a second in vitro tissue sample showing a second lesion made experimentally therein.
Figure 12B:
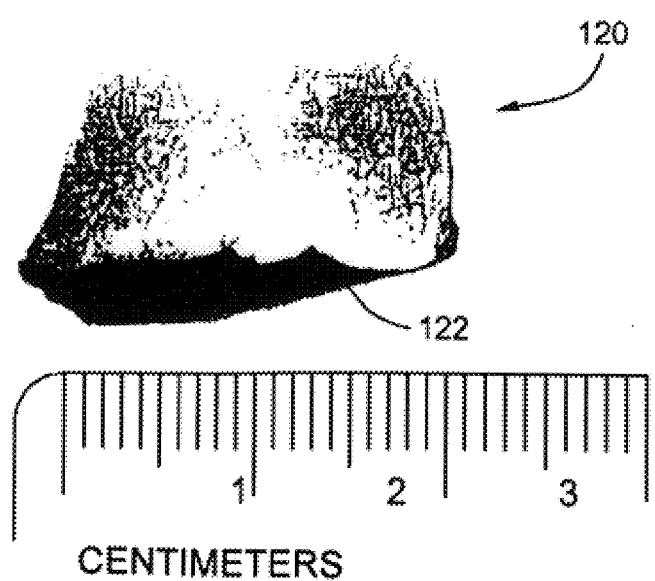

FIG. 12a is a perspective view of a second tissue sample 120 in accordance with the second line 102b of the data chart 100 of FIG. 10. Here, also, a second lesion 122 has a relatively regular shape about a second star portion 124. FIG. 12b is a side cross sectional view of the second tissue sample 110 showing the depth of the second lesion as is recorded in the second line 102b of the data chart 100 of FIG. 10.

Figure 14A:
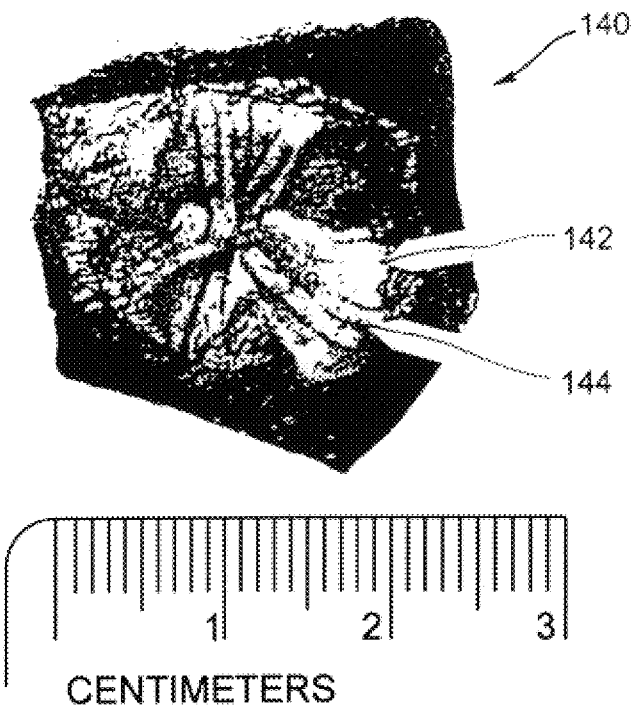
FIG. 14a is a perspective view of a fourth in vitro tissue sample showing a fourth lesion made experimentally therein.
Figure 14B:
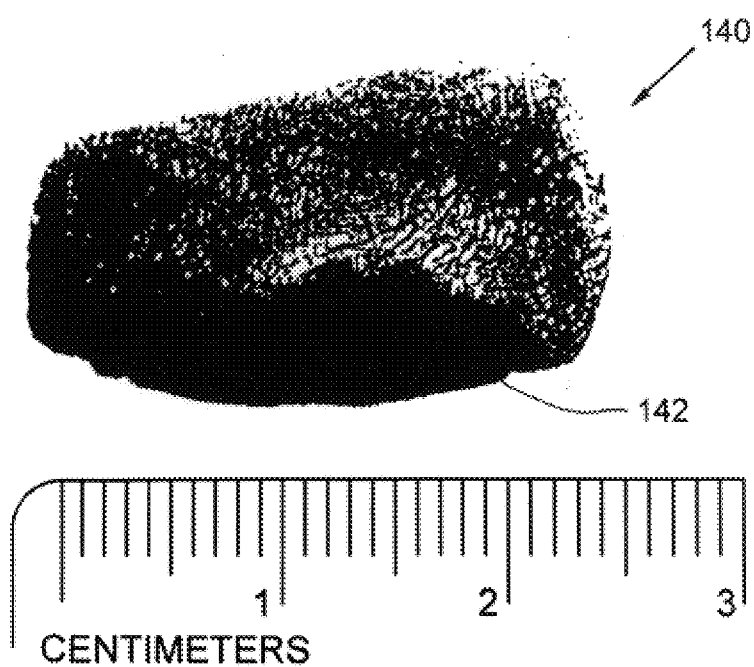
Figure 15A:
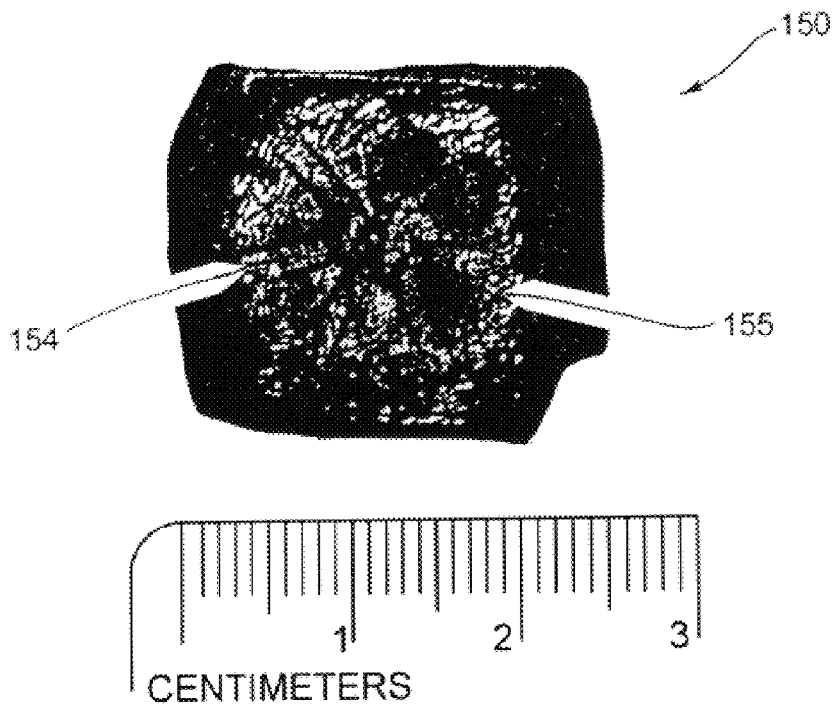
FIG. 15a is a perspective view of a fifth in vitro tissue sample showing a fifth lesion made experimentally therein.
Figure 15A:
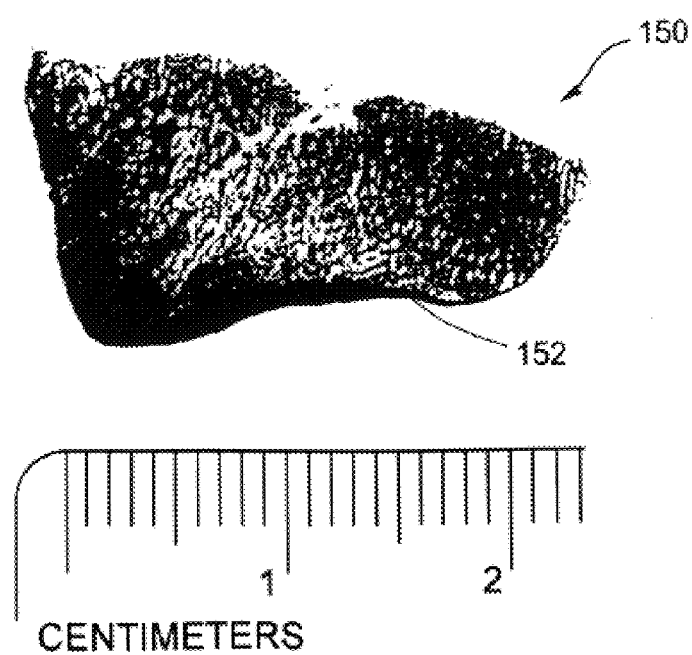

Similarly, FIG. 13a is a perspective view, and FIG. 13b is a side cross sectional view, each of a third tissue sample 130 in accordance with the third line 102c of the data chart 100 (FIG. 10); FIG. 14a is a perspective view, and FIG. 14b is a side cross sectional view, each of a fourth tissue sample 140 in accordance with the fourth line 102d of the data chart 100 (FIG. 10); and FIG. 15a is a perspective view, and FIG. 15b is a side cross sectional view, each of a fifth tissue sample 150 in accordance with the fifth line 102e of the data chart 100 (FIG. 10).

A review of FIGS. 10 through 15b will reveal that the results with the generator settings set at 80 W and 120 s (seconds) are generally consistent, with lesion diameters measuring form 14.0 mm to 16.2 mm and lesion depths measuring from 6.7 mm to 8.5 mm.

Figure 16:
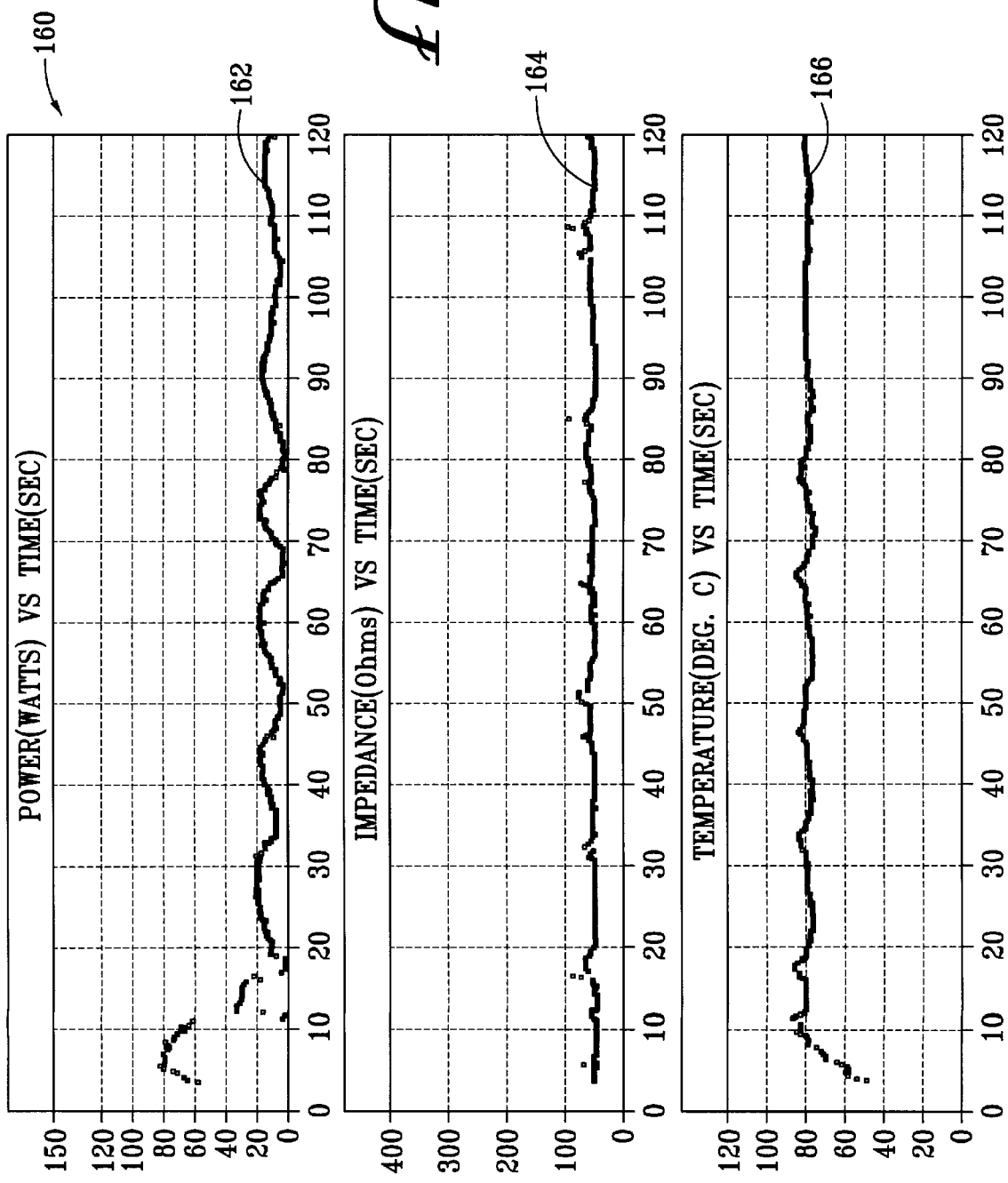
FIG. 16 is a time line chart showing the power, impedance and temperature of the inventive expandable electrode catheter over time during the course of the experiment shown in FIGS. 11a and 11b.

FIG. 16 is a first time line graph 160 showing the power 162 dissipated at the electrode structure 28 (FIG. 3), the impedance 164 of the collapsible electrode catheter assembly 10 (FIG. 1) and the instantaneous temperature 166 over the time (120 seconds) during which power was applied during the experiment described in the first line 102a of the data chart 110 and illustrated by FIGS. 11a and 11b.

Figure 17:
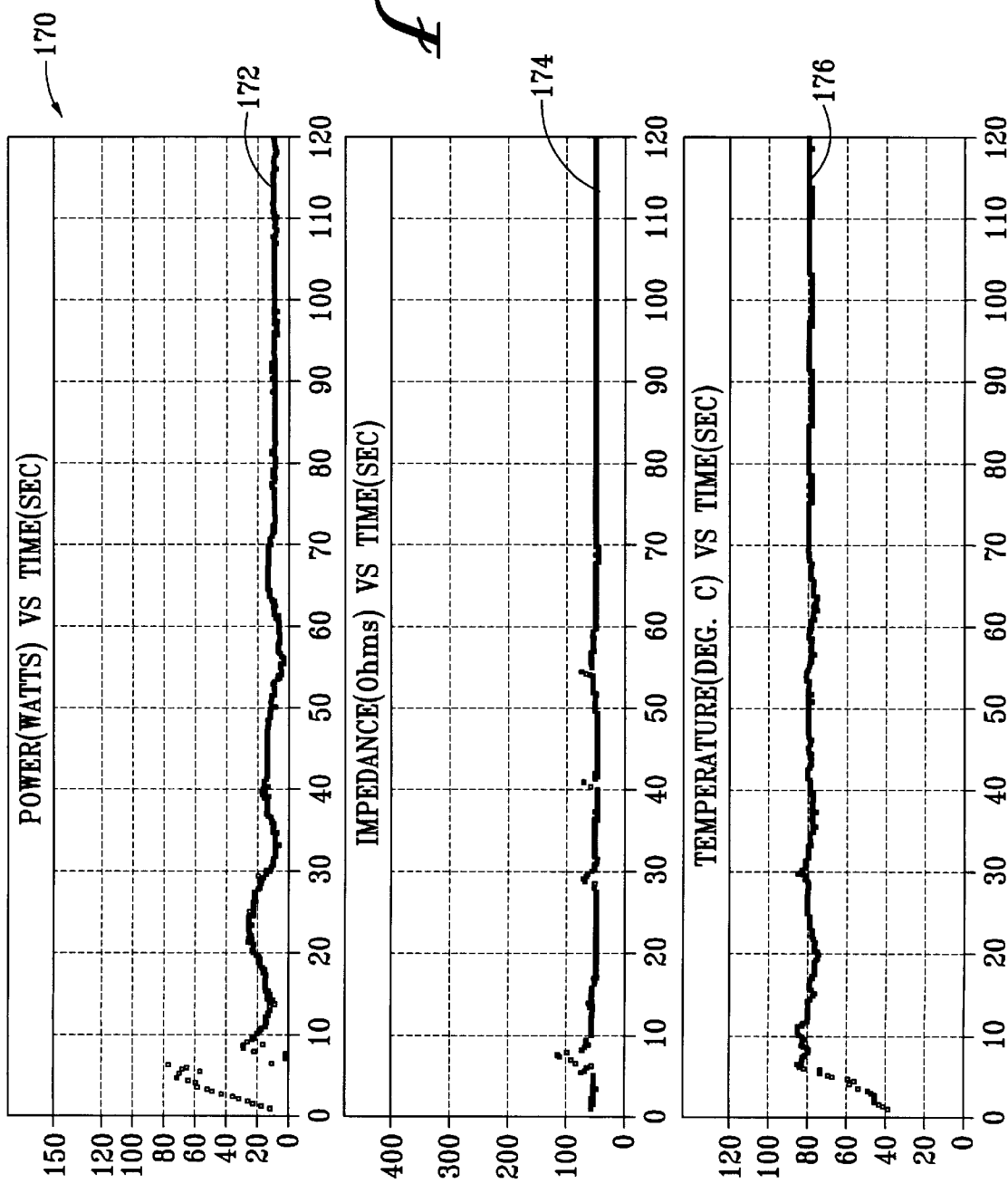
FIG. 17 is a time line chart showing the power, impedance and temperature of the inventive expandable electrode catheter over time during the course of the experiment shown in FIGS. 12a and 12b.
Figure 18:
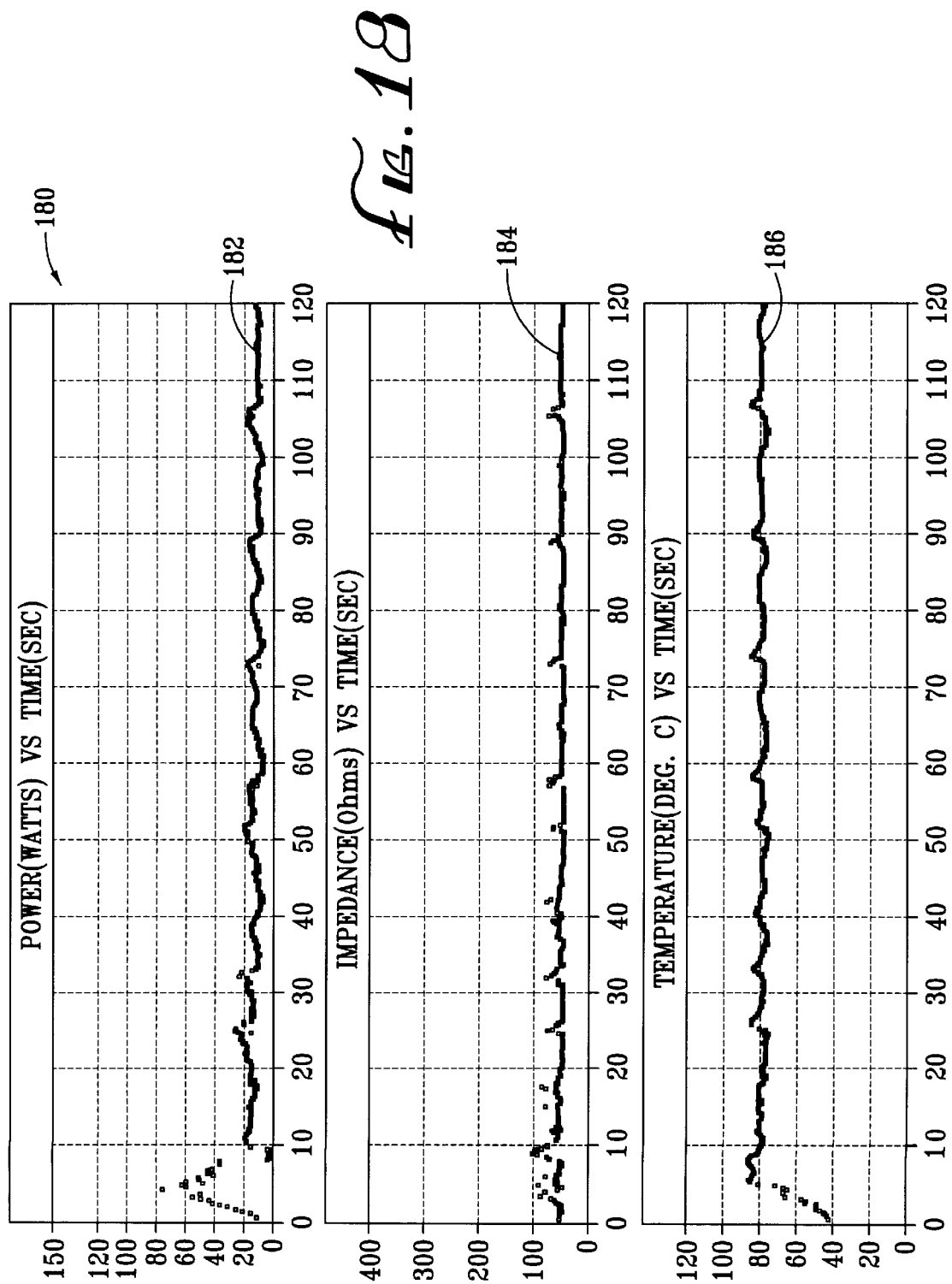
FIG. 18 is a time line chart showing the power, impedance and temperature of the inventive expandable electrode catheter over time during the course of the experiment shown in FIGS. 13a and 13b.
Figure 19:
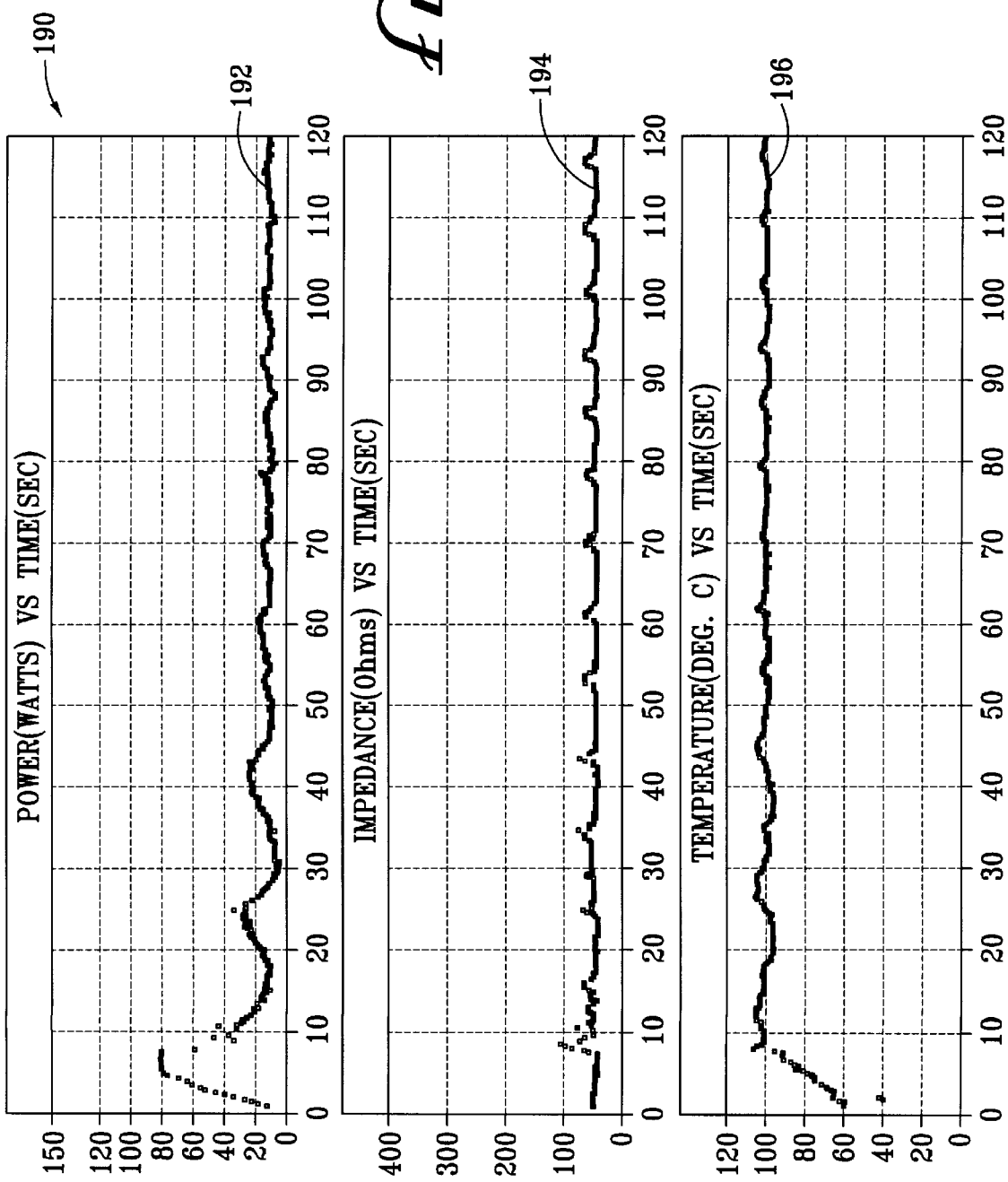
FIG. 19 is a time line chart showing the power, impedance and temperature of the inventive expandable electrode catheter over time during the course of the experiment shown in FIGS. 14a and 14b.

Similarly, FIG. 17 is a second time line graph 170 showing the power 172 dissipated, the impedance 174 and the instantaneous temperature 176 over the time relating to the experiment described in the second line 102b of the data chart 110 and illustrated by FIGS. 12a and 12b; FIG. 18 is a third time line graph 180 showing the power 182 dissipated, the impedance 184 and the instantaneous temperature 186 over the time relating to the experiment described in the third line 102c of the data chart 110 and illustrated by FIGS. 13a and 13b; FIG. 19 is a fourth time line graph 190 showing the power 192 dissipated, the impedance 194 and the instantaneous temperature 196 over the time relating to the experiment described in the fourth line 102d of the data chart 110 and illustrated by FIGS. 14a and 14b; and FIG. 20 is a fifth time line graph 2000 showing the power 202 dissipated, the impedance 204 and the instantaneous temperature 206 over the time relating to the experiment described in the fifth line 102d of the data chart 110 and illustrated by FIGS. 15a and 125b.

As described herein, the collapsible ablation structures may be manipulated from a low profile to an enlarged surface, may ablate specific locations—such as along the sinus node for sinus node modifications, in the coronary sinus for various accessory pathway ablations, and around the slow zone of the tricuspid isthmus for atrial flutter or AV node slow pathway ablations, along the IVC to SVC region for right-sided atrial fibrillation, intersecting the pulmonary veins for left-sided atrial fibrillation, and along the surface of the left ventricle for monomorphic VT. Accordingly, it is expected that the present inventive method and means will provide a significant contribution to the field and will be widely accepted and adapted for the applications described and others.

All of the above are only some of the examples of available embodiments of the present invention. Those skilled in the art will readily observe that numerous other modifications and alterations may be made without departing from the spirit and scope of the invention. Accordingly, the above disclosure is not intended as limiting and the appended claims are to be interpreted as encompassing the entire scope of the invention.

What is claimed is:

1. A device for forming lesions in tissue within the body, comprising:
   a catheter end assembly having a generally tubular main body;
   a generally tubular expanding portion having a guide collar at a proximal portion thereof slidably attached to said main body;
   an electrode structure adapted to transmit electrical energy to body tissue in order to form a lesion therein and carried by said expanding portion such that expansion of said expanding portion causes the electrode structure to effectively expand; and
   a balloon structure within said expanding portion such that expansion of said balloon structure causes said expanding portion to expand and said guide collar to slide linearly along said main body.

2. The device of claim 1, wherein:
   said expanding portion has a plurality of elongated slits therein alternating with a like plurality of elongated splines, such that expansion of said balloon structure causes the splines to move apart from each other.

3. The device of claim 2, wherein:
   said electrode structure is a conductive coating at least partially covering the exterior of the splines.

4. The device of claim 2, wherein:
   the quantity of splines is eight.

5. The device of claim 1, and further including:
   said catheter end assembly having a proximal end and a catheter tube affixed to said proximal end of said catheter end assembly for guiding said catheter end assembly.

6. The device of claim 1, and further including:
   at least one sensor positioned on said expanding portion for providing data relating to the instantaneous temperature of tissue contacting said catheter end assembly.

7. The device of claim 1, wherein:
   said electrode structure includes a plurality of individual electrodes distributed on said expanding portion.

8. The device of claim 1, wherein:
   at least a portion of said expanding portion is constructed from material having a shape memory such that inflation and deflation of said balloon structure will cause said expanding portion to first expand and then contract.

9. The device of claim 1, wherein:
   said generally tubular expanding portion includes a distal end and said balloon structure is affixed to said distal end of said generally tubular expanding portion.

10. An improved catheter, comprising:
    a handle;
    a main body tube having a proximal end engaged to said handle and a distal end;
    a distal end assembly extending from said distal end of said main body tube and including a generally tubular main body;
    an expandable end assembly having a guide collar at a proximal portion thereof slidably attached to said main body of the distal end assembly;
    an expandable electrode adapted to transmit electrical energy to body tissue in order to form a lesion therein and carried by said expandable end assembly such that expansion of said expandable end assembly enlarges an effective surface of said expandable electrode; and
    a balloon interior to said expandable end assembly such that inflation of said balloon causes said expandable end assembly to expand and said guide collar to slide linearly alone said main body of the distal end assembly.

11. The improved catheter of claim 10, wherein:
    said expandable end assembly includes a generally tubular structure having a plurality of longitudinal slits therein and a like plurality of longitudinal splines separated by the slits such that expansion of said balloon causes the splines to be urged apart at the slits.

12. A device for forming lesions in tissue within a chamber of the body, comprising:
    a catheter end assembly having a generally tubular main body;
    a generally tubular expanding portion having a proximal portion attached to said main body and a plurality of elongated slits therein alternating with a like plurality of elongated splines;
    an inflatable balloon structure within said expanding portion, such that expansion of said balloon structure causes said expanding portion to expand and said splines to move apart from each other;
    an electrode structure adapted to transmit electrical energy to body tissue in order to form a lesion therein, and carried by said expanding portion such that expansion of said expanding portion causes the electrode structure to effectively expand; and wherein said expanding portion is sized, such that expansion of said expanding portion within the body chamber causes said electrode structure to be placed in substantial circumferential contact with the tissue of the body chamber.

13. The device of claim 12, wherein:

said electrode structure is a conductive coating at least partially covering the exterior of the splines.

14. The device of claim 12, wherein:

the quantity of splines is eight.

15. The device of claim 12, wherein:

said electrode structure includes a plurality of individual electrodes distributed on said expanding portion.

16. The device of claim 12, wherein a proximal end of said expanding portion has a guide collar slidably attached to said main body, said guide collar sliding linearly along said main body when said expanding portion is expanding.

* * * * *